(12) United States Patent
Zabetakis et al.

(10) Patent No.: US 10,611,809 B2
(45) Date of Patent: Apr. 7, 2020

(54) SINGLE-DOMAIN ANTIBODY FUSION PROTEINS WITH THE ACID TAIL OF ALPHA-SYNUCLEIN

(71) Applicant: The Government of the United States of America, as represented by the Secretary of the Navy, Arlington, VA (US)

(72) Inventors: Daniel Zabetakis, Brandywine, MD (US); George P. Anderson, Bowie, MD (US); Ellen R. Goldman, Germantown, MD (US); Kendrick Turner, Washington, DC (US); P. Audrey Brozozog Lee, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/365,900

(22) Filed: Mar. 27, 2019

(65) Prior Publication Data

US 2019/0211068 A1 Jul. 11, 2019

Related U.S. Application Data

(62) Division of application No. 14/158,208, filed on Jan. 17, 2014, now Pat. No. 10,294,283.

(51) Int. Cl.
| | | |
|---|---|---|
| *C07K 16/00* | (2006.01) | |
| *C07K 14/47* | (2006.01) | |
| *C07K 16/12* | (2006.01) | |
| *C07K 16/16* | (2006.01) | |

(52) U.S. Cl.
CPC .......... *C07K 14/47* (2013.01); *C07K 16/1271* (2013.01); *C07K 16/1278* (2013.01); *C07K 16/16* (2013.01); *C07K 2317/569* (2013.01); *C07K 2317/94* (2013.01); *C07K 2319/00* (2013.01)

(58) Field of Classification Search
None
See application file for complete search history.

(56) References Cited

U.S. PATENT DOCUMENTS

2005/0203010 A1* 9/2005 Kim ...................... C07K 14/47
530/350

OTHER PUBLICATIONS

Swain et al. Analytical Biochemistry, vol. 417, pp. 188-194, 2011, (Year: 2011).*
De Genst et al. J. Mol. Biol. vol. 402, pp. 326-343, 2010. (Year: 2010).*

* cited by examiner

*Primary Examiner* — Gary B Nickol
*Assistant Examiner* — Khatol S Shahnan Shah
(74) *Attorney, Agent, or Firm* — US Naval Research Laboratory; Roy Roberts

(57) ABSTRACT

A single-domain antibody (sdAb) is produced by causing a bacteria to express the sdAb into cytoplasm of the bacteria, wherein the sdAb is expressed as a fusion protein with the acid tail of α-synuclein. In embodiments, the protein is free of a periplasmic location tag. Such antibodies have the unexpected ability to refold after thermal denaturation.

8 Claims, 6 Drawing Sheets

Specification includes a Sequence Listing.

SINGLE-DOMAIN ANTIBODY FUSION PROTEINS WITH THE ACID TAIL OF ALPHA-SYNUCLEIN

BACKGROUND

A need exists for single-domain antibodies having improved ability to refold following thermal denaturation.

BRIEF SUMMARY

In one embodiment, a fusion protein includes a single-domain antibody (sdAb) and the acid tail of α-synuclein. In further embodiments, the fusion protein is free of a periplasmic location tag.

BRIEF DESCRIPTION OF THE DRAWINGS

FIG. 1A shows the optical density (OD) absorbance at 280 nm (OD280) of sdAb H1 and C8 with and without the ATS, measured after heating for 1 hour at a concentration of 1 mg/ml at the indicated temperatures. Percentage OD280 versus unheated preparations are plotted for each temperature. FIG. 1B shows the percent binding ability of the H1 and H1-ATS samples as measured by surface plasmon resonance (SPR), shown in response units (RU). Whereas the H1-ATS was soluble at all temperatures, it lost activity on heating as judged by the reduction of signal versus the RT sample.

FIG. 3A shows melting and cooling curves for the sdAb A3-ds construct; the fusion of the sdAb A3-ds with the ATS is shown in FIG. 3B. Heating curves are dashed and cooling in solid line.

FIG. 4A shows heating and cooling of sdAb A3 that was produced in the cytoplasm and FIG. 4B shows the curves form sdAb A3-ATS.

FIG. 5A shows the heating and cooling of cytoplasmically produced sdAb A5. FIG. 5B shows the first heating and cooling cycle of sdAb A5-ATS produced in the cytoplasm where FIG. 5C shows the second heating and cooling cycle from this material.

DETAILED DESCRIPTION

Definitions

Figure 1A:
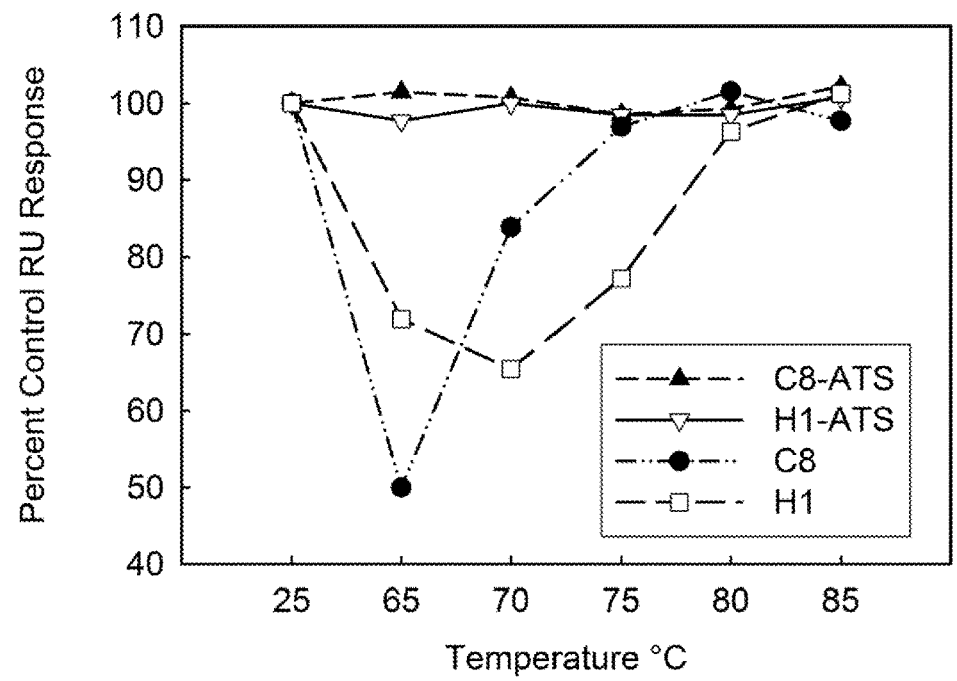
FIGS. 1A and 1B show representative data that demonstrated the improved solubility of the H1 and C8 sdAb variants with acid tail of α-synuclein (ATS) versus the wild-type constructs.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Description

Single-domain antibodies (sdAbs) are recombinant derivatives of heavy-chain-only antibodies found in camelids and sharks. Heavy-chain-only antibodies are distinct from conventional antibodies in that they lack the typical heavy-chain/light-chain structure. The binding element for conventional antibodies is composed of both a heavy-chain variable domain and light-chain variable domain so that the functional component of the antibody is divided between two distinct proteins. By contrast, the binding element of a heavy-chain-only antibody is composed of a single domain. This confers two features that have been exploited. First, this binding domain can be isolated from the heavy-chain and used as a very small (~15 kDa) functional protein by itself. Secondly, as compared to a conventional antibody, the lack of posttranslational modifications in sdAbs allows for their production in bacterial expression systems rather than more complex and costly eukaryotic systems.

Basic structure, composition, preparation, and uses of relevant antibodies are described in, for example, U.S. Pat. Nos. 5,800,988; 5,840,526; 5,874,541; 6,005,079; 6,015,695; and 6,765,087.

Bacterial expression is a favorable means of producing recombinant proteins in large quantities. Typically, sdAbs are produced with a periplasmic localization tag. This short amino-acid sequence, placed at the amino-terminus of the protein, directs the bacterial cell to export the protein from the cytoplasm into the periplasmic space (the space between the inner and outer membranes in bacteria such as *E. coli*). This has two benefits. First, proteins can be extracted from the periplasm without need to fully lyse the cells. Second, the periplasm is a more favorable environment for the formation of disulfide bonds in exogenous proteins.

Living bacteria normally have a difference in redox potential between the cytoplasm, which is reducing, and the periplasm, which is oxidizing. A reducing environment tends to cleave disulfide bonds. Therefore, if the non-native protein of interest contains disulfide links, then cytoplasmic expression is unfavorable. This is typically the case with sdAbs, which normally contain a single disulfide that contributes to thermal stability. On the other hand, periplasmic expression introduces a significant bottleneck in protein production (the export through the inner membrane) and usually results in significantly lower yield compared to expression in the cytoplasm. It would be beneficial to ameliorate the effects of cytoplasmic expression in order to benefit from increased protein production.

However, sdAb expression in the reducing cytoplasm is prone to detrimental effects. In proteins that would form disulfide bonds (including most sdAbs), there is a reduction of the melting temperature of the protein (i.e., the temperature at which the protein, in water, unfolds into a random coil) due to the lack of disulfide bonding. When sdAbs lack the disulfide bond, they do not refold on cooling after thermal denaturation. While lowering the melting temperature is undesirable, a loss of refolding imposes a severe limitation on the utility of sdAb.

As disclosed herein, a solution to the problem of refolding of cytoplasmically expressed sdAb using the acid tail of α-synuclein (ATS). The synucleins are a class of human proteins, and α-synuclein has been implicated in the pathology of Parkinson's disease. This protein is a small heat shock protein (sHSP), a class of proteins that function to prevent the aggregation of other proteins within the cell during periods of biochemical stress.

The ATS has been used in isolation and as fusions to other proteins to prevent aggregation and to protect proteins from damage by freeze-thaw cycles. It has also been used to stabilize proteins against thermal denaturation.

Critically, however, reports to date found that ATS was not able to promote refolding after thermal denaturation of enzymes. See refs. 5 and 6. Thus, the results described herein, with the ATS tail significantly assisting refolding sdAbs, was surprising and unexpected. Providing refolding ability to sdAbs presents many improved opportunities for commercialization. For example, diagnostic and/or analytical kits and devices may be used in the field use where refrigeration is not available.

Constructs of sdAbs

The sdAb used were isolated from immune-based libraries of phage-displayed llama sdAb. The protein sequence of the ATS tail used DPDNEAYEMPSEEGYQDYEPEA (SEQ ID No: 1). Conventional molecular biological techniques were used to generate constructs. Proteins were produced in *E. coli* with polyhistidine tails to assist purification, and purified using an osmotic shock protocol followed by purification through a standard immobilized metal affinity (IMAC) protocol. Size exclusion chromatography was used as a final purification step, and the protein concentration was estimated by absorbance at 280 nm using a nanodrop spectrophotometer. Growth and purification of the cytoplasmically produced proteins was performed overnight at 16° C. The cells were broken by chemical means and/or sonication and then the protein purified by IMAC and size exclusion chromatography.

The ATS sequence was added to the C-terminus of certain sdAbs. The sdAbs used were sdAb A5, a sdAb specific for the Bcl A protein of the *Bacillus anthracia* spore, sdAb H1 and C8, which recognize ricin, and sdAb A3, which binds Staphylococcal Enterotoxin B (SEB).

The sequences of these proteins and their ATS fusions were as follows:

```
C8-ATS:
                                        (SEQ ID No: 2)
EVQLQASGGGLVQGGDSLRLSCAASGRTLGDYGVAWFRQAPGKEREFVS

VISRSTIITDYANSVKGRFTISRDNAKNAVYLQMNSLKPEDTAVYYCAVI

ANPVYATSRNSDDYGHWGQGTQVTVSSAAADPDNEAYEMPSEEGYQDYE

PEALEHHHHHH

C8
                                        (SEQ ID No: 3)
EVQLQASGGGLVQGGDSLRLSCAASGRTLGDYGVAWFRQAPGKER

EFVSVISRSTIITDYANSVKGRFTISRDNAKNAVYLQMNSLKPEDTAV

YYCAVIANPVYATSRNSDDYGHWGQGTQVTVSSAAALEHREIHREI
```

-continued

```
A3-ATS:
                                        (SEQ ID No: 4)
EVQLVESGGGLVQAGDSLRLSCTASGRTFSRAVMGWFRQAPGKEREFVA

AISAAPGTAYYAFYADSVRGRFSISADSAKNTVYLQMNSLKPEDTAVYYC

AADLKMQVAAYMNQRSVDYWGQGTQVTVSSAAADPDNEAYEMPSEEG

YQDYEPEALEHHHHHH

A3:
                                        (SEQ ID No: 5)
EVQLVESGGGLVQAGDSLRLSCTASGRTFSRAVMGWFRQAPGKEREFVA

AISAAPGTAYYAFYADSVRGRFSISADSAKNTVYLQMNSLKPEDTAVYYC

AADLKMQVAAYMNQRSVDYWGQGTQVTVSSAAALEHHHHHH

A5-ATS:
                                        (SEQ ID No: 6)
EVQLQASGGGLVQPGGSLRLSCVASGINFSTNVPTWYRQAPGKQRELVAV

ITTNGLTRYADSVKGRFTISKDNAKNAVYLQMNSLKPEDTAVYYCRARD

YWGQGTQVTVSSEPKTPKPQPAASGAEFAAADPDNEAYEMPSEEGYQD

YEPEALEHHHHHH

A5:
                                        (SEQ ID No: 7)
EVQLQASGGGLVQPGGSLRLSCVASGINFSTNVPTWYRQAPGKQRELVAV

ITTNGLTRYADSVKGRFTISKDNAKNAVYLQMNSLKPEDTAVYYCRARD

YWGQGTQVTVSSEPKTPKPQPAASGAEFAAALEHHHHHH

H1-ATS:
                                        (SEQ ID No: 8)
DVQLQASGGGLAQAGGSLRLSCAYSGDTVNDYAMAWFRQAPGKGREFV

AAIRARGGGTEYLDSVKGRFTISRDNGENTAYLQMDNLQPDDTALYFC

ALAMGGYAYRAFERYSVRGQGTQVTVSSAAADPDNEAYEMPSEEGYQD

YEPEALEHHHHHH

H1:
                                        (SEQ ID No: 9)
DVQLQASGGG LAQAGGSLRL SCAYSGDTVN DYAMAWFRQA

PGKGREFVAA IRARGGGTEY LDSVKGRFTI SRDNGENTAY

LQMDNLQPDD TALYFCALAM GGYAYRAFER

YSVRGQGTQVTVSSAAALEHHHHHH
```

Experimental Methods

Heating of the sdAb constructs to various temperatures and time points was done at a concentration of 1 mg/ml using a thermal cycler. After heating, the samples were removed from the thermal cycler, cooled to room temperature on the bench top, centrifuged and protein concentration measured by absorbance at 280 nm.

Melting temperature and ability to refold was determined by circular dichroism (CD). Measurements were performed using a spectropolarimeter equipped with a temperature control system. CD spectra were obtained from 200 to 245 nm and melting point data was acquired at a single wavelength between 200 and 205 nm, at a temperature rate of 2.5° C./min.

Surface plasmon resonance (SPR) was used to measure binding kinetics of sdAb wild-type and ATS variants as well as to assay their binding activity after heating. Measurements were performed on a ProteON XPR36 (Bio-Rad) using a chip coated with appropriate antigens (iBcl A, SEB, or ricin) at 20 μg/mL. Binding was assessed by flowing six concentrations varying from 0-300 nM at 50 μL/min for 120 s over the antigen coated chip and then monitoring dissociation for 600 s. The chip was regenerated using 50 mM glycine-HCl (pH 2.0) for 36 s, prior to any additional testing. The data were analyzed with the ProteON Manager 2.1 software, corrected by subtraction of the zero antibody concentration column as well as interspot corrected. Binding constants were determined using the software's Langmuir model. When assessing the ability of the A3 and A3-ATS constructs to bind antigen after heating, samples were heated to 90° C. at 1 mg/ml for the indicated time, and then allowed to cool to room temperature.

Experimental Results

The addition of the ATS sequence did not measurably change the affinity of any of the sdAb for their targets, although it did shift the melting temperature slightly lower. The level of production of fusion proteins was somewhat lower than that of the parental sdAb, however protein production of the fusion could potentially be optimized by changing the growth and production protocol. The ATS was added to sdAb A5, which included part of the upper hinge region, which contains several positively charged amino acids, and to clones H1, C8, and A3 which do not include the hinge sequence.

Figure 1B:
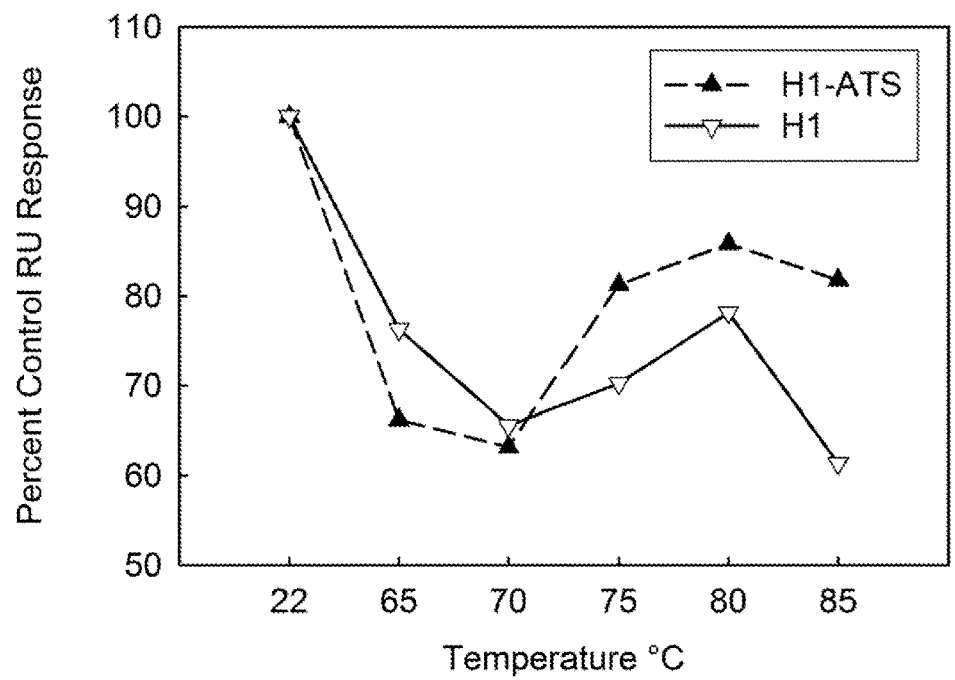

The sdAb-ATS fusions demonstrated an increase in the solubility over parental sdAb when they were heated at high concentration (1 mg/ml) above their melting temperature, with protein concentration estimated by absorbance at 280 nm. FIG. 1 shows representative data that demonstrates the improved solubility of the H1 and C8 sdAb variants with ATS tails versus the wild-type constructs. Interestingly, sdAb lacking the ATS often have a greater tendency to aggregate and fall out of solution when heated within 5-10° C. of their Tm than when they are heated 20° C. above their Tm. As seen in FIG. 1B, the ability of the H1 and C8 sdAb-ATS fusions to function after heating did not track with the solubility, using surface plasmon resonance (SPR) to measure binding to an appropriate antigen. When heated ~20° C. above their Tm the sdAb were more soluble than when heated within ~10° C. above their Tm, but not more functional.

Figure 2:
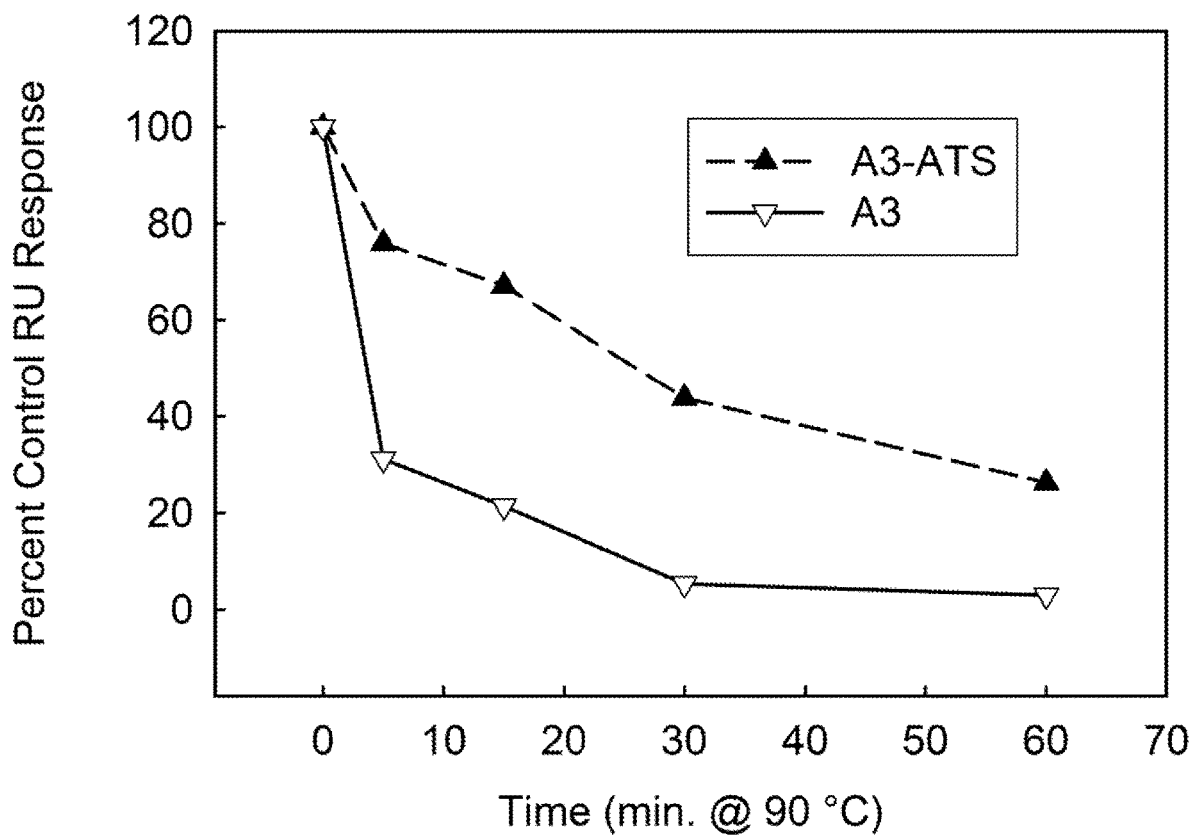
FIG. 2 shows binding ability of sdAb A3 with and without the ATS tail, as determined by SPR. The sdAb A3 constructs were heated to 90° C. for the indicated periods of time, up to 60 minutes, and then their binding to a SEB coated surface was assessed by SPR. The percentage of the unheated signal is plotted for both the sdAb A3 and sdAb A3-ATS constructs.

Some of the most dramatic improvements in stability were recorded with sdAb A3. This clone has a melting temperature of ~85° C., and showed refolding when examined by CD. When heated at high concentration, however, sdAb A3 is prone to aggregation; after heating at a concentration of 1 mg/ml for thirty minutes at 90° C., the clone had lost its binding ability. The sdAb A3 variant with the ATS retains a significant portion of its binding activity even after heating (1 mg/ml) for an hour at 90° C., as shown in FIG. 2.

Variable heavy domains normally contain a conserved disulfide bond between the framework 1 and framework 3 regions of the protein. Removal of this conserved disulfide through mutagenesis of the two cysteines has previously been reported to result in a decrease of the melting temperature of the sdAb. Such variations (C22A/C99V) in the A3 and A3-ATS proteins were made, with the following sequences:

A3-ds:
(SEQ ID No: 10)
EVQLVESGGGLVQAGDSLRLSATASGRTFSRAVMGWFRQAPGKEREFVA

AISAAPGTAYYAFYADSVRGRFSISADSAKNTVYLQMNSLKPEDTAVYYV

AADLKMQVAAYMNQRSVDYWGQGTQVTVSSAAALEHHHHHH

-continued

A3-ds-ATS:
(SEQ ID No: 11)
EVQLQASGGGLVQPGGSLRLSAVASGINFSTNVPTWYRQAPGKQRELVAV

ITTNGLTRYADSVKGRFTISKDNAKNAVYLQMNSLKPEDTAVYYVRARD

YWGQGTQVTVSSEPKTPKPQPAASGAEFAAADPDNEAYEMPSEEGYQD

YEPEALEHHHHHH

Figure 3A:
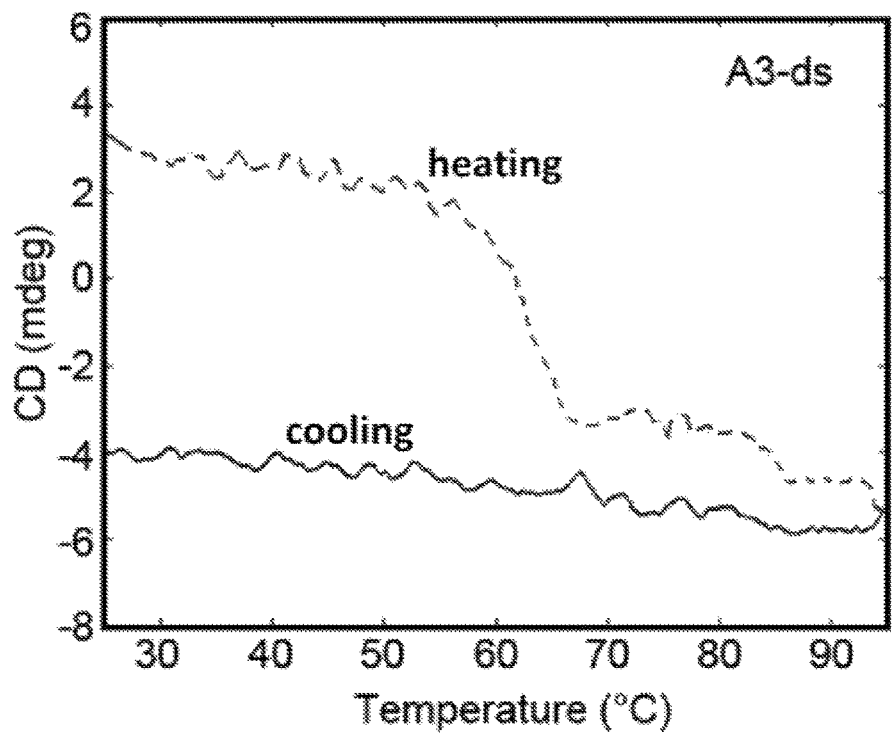
FIGS. 3A and 3B show heating and cooling curves of sdAb A3 lacking the disulfide (A3-ds) with and without the ATS measured by CD.
Figure 3B:
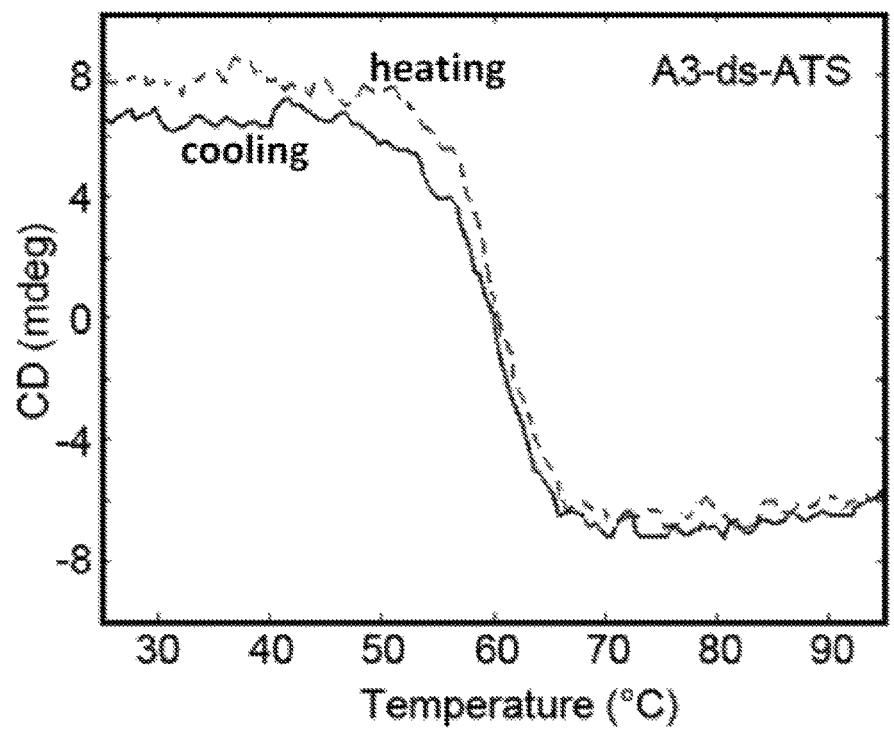

As seen in FIGS. 3A and 3B, this mutation was also found to lead to the inability of the resultant mutant to refold after heat denaturation. When the disulfide was removed from sdAb A3 through mutagenesis, its ability to bind antigen was unchanged however its melting temperature dropped about 20° C., and it was no longer able to refold after heating. When the disulfide free version of sdAb A3 was expressed as a fusion with the ATS tail (A3-ds-ATS), its affinity towards SEB was unchanged and the melting temperature remained low, but its ability to refold was restored. Similar results were observed with sdAb A5 (data not shown).

The sequences for the A3 and A5 sdAb, with and without the ATS, were mobilized to vectors for expression in the cytoplasm. Much of the cytoplasmically produced sdAb lacks the disulfide bond, as inferred from its decreased melting temperature. As mutants lacking cysteines were able to refold when expressed with the ATS tail, it seemed possible that the tail would promote refolding of sdAb expressed in the cytoplasm.

Figure 4A:
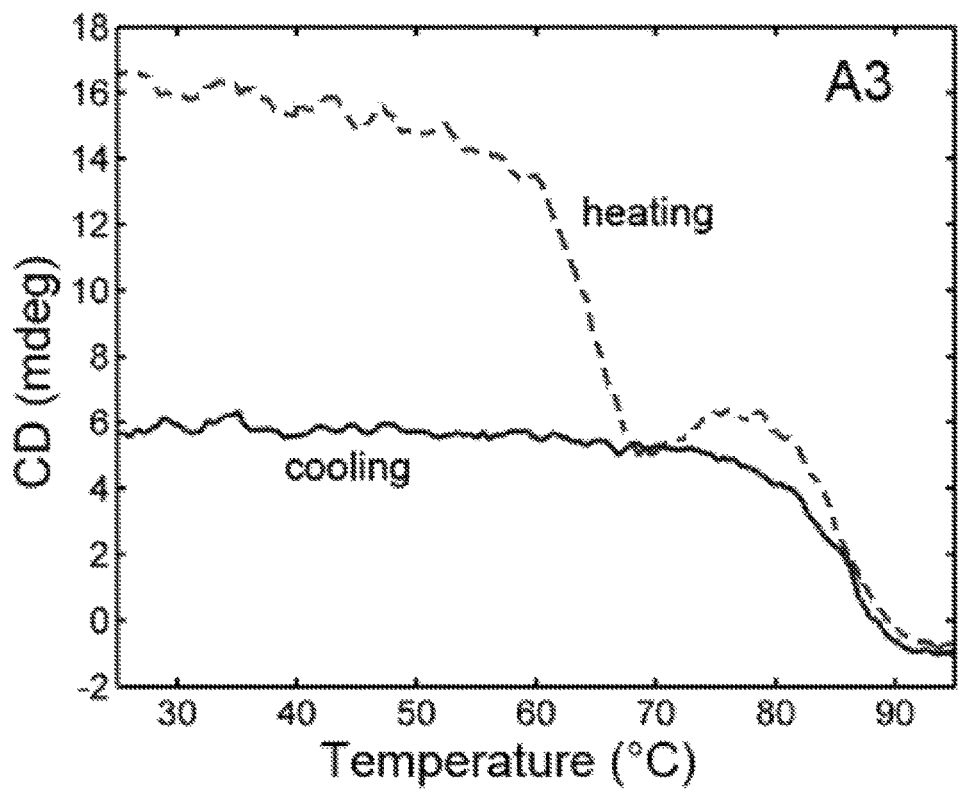
FIGS. 4A and 4B show melting and refolding of cytoplasmically expressed sdAb A3 and sdAb A3-ATS as measured by circular dichroism (CD).
Figure 4B:
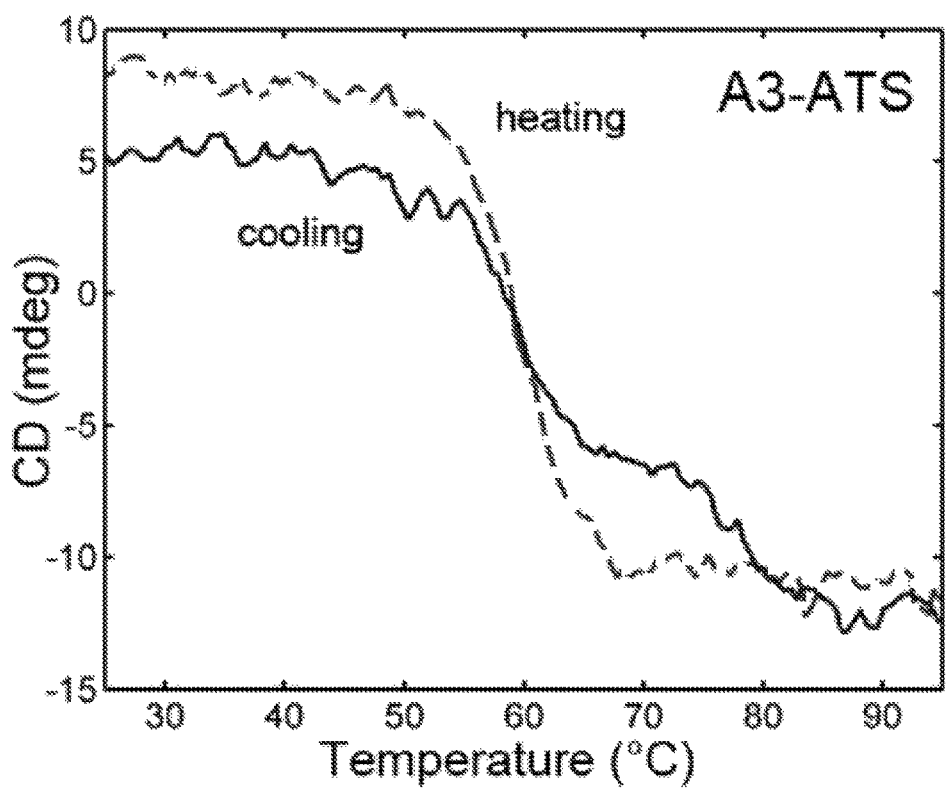
Figure 5A:
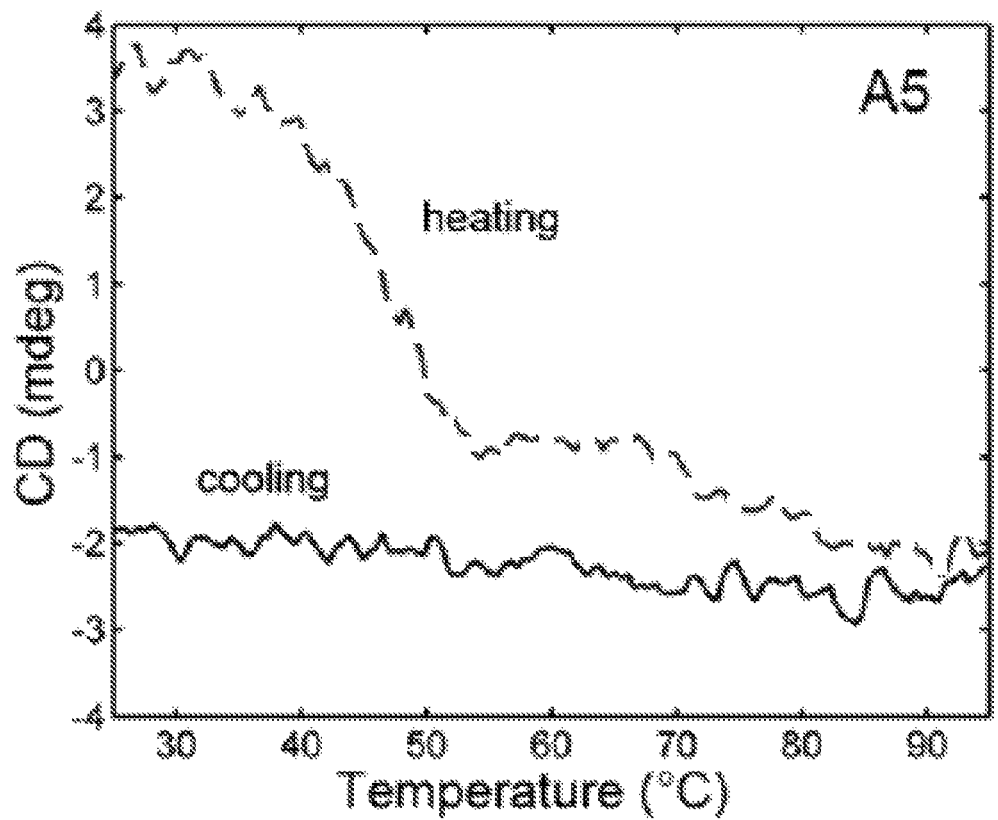
FIGS. 5A, 5B, and 5C show melting and refolding of sdAb A5 and sdAb A5-ATS from cytoplasmic expression, as determined by CD.
Figure 5B:
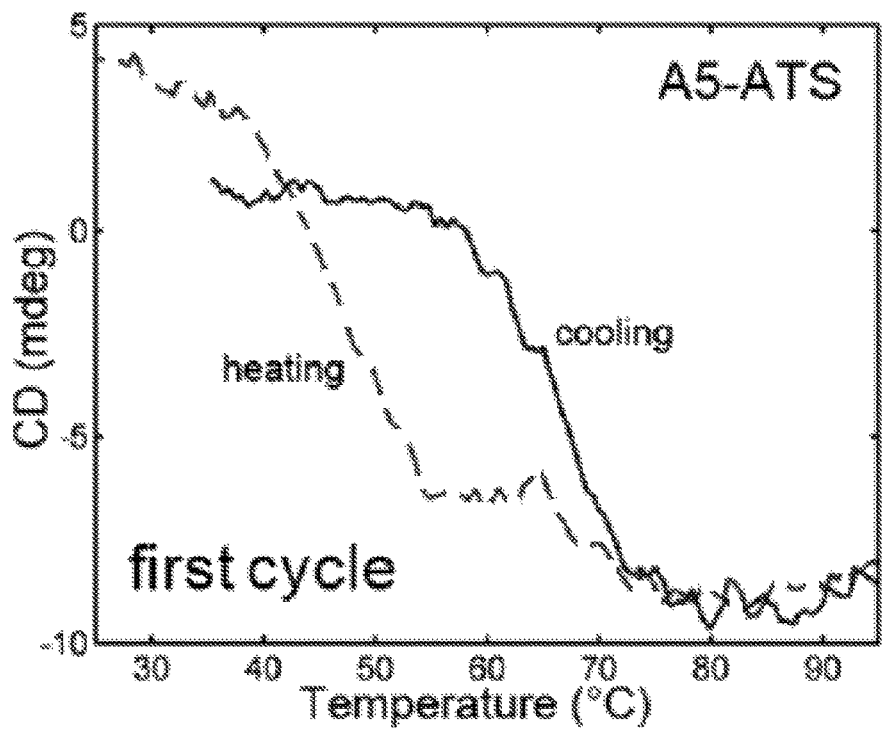
Figure 5C:
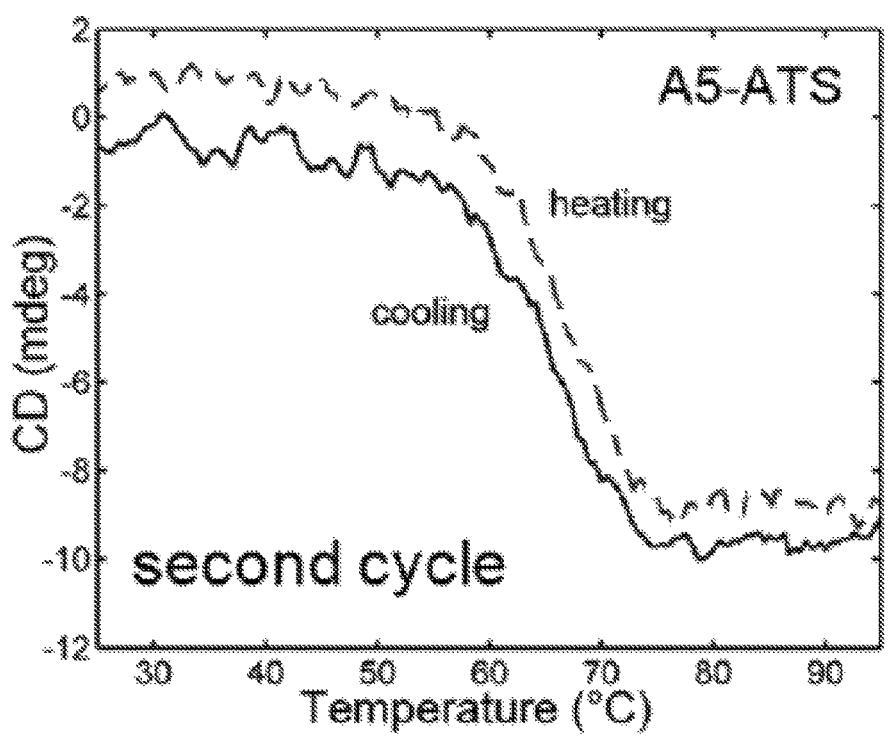

The melting and refolding of sdAb A3 and sdAb A3-ATS expressed in the cytoplasm was examined. Two melting transitions were observed in the cytoplasmically expressed A3 which can be attributed to sdAb populations with and without a formed disulfide (FIG. 4A). The majority of the preparation of wild-type sdAb-A3 expressed in the cytoplasm did not refold; only the component with the higher Tm appeared to have refolding ability. The cytoplasmically produced variant with the ATS showed a melting transition almost exclusively at the lower temperature. On cooling, the A3 with the ATS was able to refold almost completely; with a portion refolded at the higher melting temperature associated with disulfide containing protein, and the rest refolded at the lower temperature associated with protein lacking disulfides (FIG. 4B). FIGS. 5A-5C show melting curves from sdAb A5 and sdAb A5-ATS expressed in the cytoplasm. The A5 expressed in the cytoplasm had a low melting temperature and showed no refolding; the A5-ATS fusion protein melted at the expected temperature for an sdAb lacking the disulfide, however it refolded at the higher temperature that corresponds to the melting temperature of the version with an intact disulfide. Subsequent heating cycles showed melting and refolding both at the higher temperature.

Intrabodies

It is contemplated that sdAbs as described herein may have use as intrabodies, active inside cells to binding to target molecules within the cells. Intrabody-based strategies using sdAb have several potential applications including protection from intracellular toxins and viral inhibitors. In order for a sdAb to be an efficient intrabody, it must function in the absence of its disulfide. Selection strategies, such as the use of a bacterial 2-hybrid system, have been described specifically for the isolation of camelid sdAb best able to function as intrabodies. The ATS fusion potentially endows a wide variety of sdAbs with ability to function as an intrabody.

Concluding Remarks

As demonstrated, the sdAb with the ATS can be expressed in the cytoplasm to produce proteins that refold after heat denaturation. In the case of sdAb A5 ATS, once heated above its melting temperature and cooled to refold, the subsequent melting temperature of the cytoplasmically produced protein shifted higher to become identical to that of the periplasmically produced version, suggesting that the ATS tail may somehow promote disulfide formation (FIG. 5). Even when the majority of the protein melts and refolds at the lower temperature associated with no disulfide bond formation (FIG. 4), the ability of the cytoplasmically produced sdAb to refold means that the thermal stability of the sdAb is no longer limited by its melting point. The finding that the addition of the acid tail of α-synuclein promoted refolding was surprising and unexpected.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

All documents mentioned herein are hereby incorporated by reference for the purpose of disclosing and describing the particular materials and methodologies for which the document was cited.

REFERENCES

1. Eliezer (2013) "The Mysterious C-Terminal Tail of Alpha-Synuclein: Nanobody's Guess." *Journal of Molecular Biology,* Volume 425, Issue 14, 24 Jul. 2013, Pages 2397-2411
2. Holliger P, Hudson P J (2005) Engineered antibody fragments and the rise of single domains. *Nature Biotechnology* 23: 1126-1136
3. Kim, Y. M., et al. (2009) "Expression of human interferon alpha-1 with enhanced stability via the tagging system of a stabilizing peptide" *Prot. Expr. Purif.* 63, 140-146
4. Park S M, Kim J (2008) "A soluble and heat-resistant form of hantavirus nucleocapsid protein for the serodiagnosis of HFRS" *Journal of Virological Methods* 147: 1-9
5. Park, S. M., et al. (2002) "Distinct Roles of the N-terminal-binding Domain and the C-terminal-solubilizing Domain of alpha-synuclein, a Molecular Chaperone" *J. Biol. Chem.* 277, 28512-28520
6. Park, S. M., et al. (2002) "Stress-Induced Aggregation Profile of GST-alpha-Synuclein Fusion Proteins" *Biochem.* 41, 4137-4146
7. Park, S. M., et al. (2004) "Effects of novel peptides derived from the acid tail of synuclein (ATS) on the aggregation and stability of fusion proteins" *Prot. Eng. Design Sel.* 17, 251-260

What is claimed is:

1. A fusion protein comprising:
   a single-domain antibody (sdAb) and
   the acid tail of α-synuclein,
   wherein the fusion protein is free of a periplasmic location tag.

2. The fusion protein of claim 1, further comprising a cleavage site to separate the acid tail of α-synuclein.

3. The fusion protein of claim 1, further comprising an affinity tag for purification.

4. The fusion protein of claim 1, further comprising a cleavage site to separate the affinity tag.

5. The fusion protein of claim 1, wherein the affinity tag is polyhistidine.

6. The fusion protein of claim 1, wherein the acid tail of α-synuclein comprises the amino acid sequence

```
                                              (SEQ ID No: 1)
DPDNEAYEMPSEEGYQDYEPEA.
```

7. A purified protein comprising a single-domain antibody joined to the acid tail of α-synuclein.

8. The purified protein of claim 7, wherein the acid tail of α-synuclein comprises the amino acid sequence

```
                                              (SEQ ID No: 1)
DPDNEAYEMPSEEGYQDYEPEA.
```

\* \* \* \* \*

SEQUENCE LISTING

```
<160> NUMBER OF SEQ ID NOS: 11

<210> SEQ ID NO 1
<211> LENGTH: 22
<212> TYPE: PRT
<213> ORGANISM: Artificial Sequence
<220> FEATURE:
<223> OTHER INFORMATION: synthetic construct

<400> SEQUENCE: 1

Asp Pro Asp Asn Glu Ala Tyr Glu Met Pro Ser Glu Glu Gly Tyr Gln
1               5                   10                  15

Asp Tyr Glu Pro Glu Ala
            20

<210> SEQ ID NO 2
<211> LENGTH: 159
<212> TYPE: PRT
<213> ORGANISM: Artificial Sequence
<220> FEATURE:
<223> OTHER INFORMATION: synthetic construct

<400> SEQUENCE: 2

Glu Val Gln Leu Gln Ala Ser Gly Gly Gly Leu Val Gln Gly Gly Asp
1               5                   10                  15

Ser Leu Arg Leu Ser Cys Ala Ala Ser Gly Arg Thr Leu Gly Asp Tyr
            20                  25                  30

Gly Val Ala Trp Phe Arg Gln Ala Pro Gly Lys Glu Arg Glu Phe Val
        35                  40                  45

Ser Val Ile Ser Arg Ser Thr Ile Ile Thr Asp Tyr Ala Asn Ser Val
    50                  55                  60

Lys Gly Arg Phe Thr Ile Ser Arg Asp Asn Ala Lys Asn Ala Val Tyr
65                  70                  75                  80
```

-continued

Leu Gln Met Asn Ser Leu Lys Pro Glu Asp Thr Ala Val Tyr Tyr Cys
                85                  90                  95

Ala Val Ile Ala Asn Pro Val Tyr Ala Thr Ser Arg Asn Ser Asp Asp
            100                 105                 110

Tyr Gly His Trp Gly Gln Gly Thr Gln Val Thr Val Ser Ser Ala Ala
        115                 120                 125

Ala Asp Pro Asp Asn Glu Ala Tyr Glu Met Pro Ser Glu Glu Gly Tyr
130                 135                 140

Gln Asp Tyr Glu Pro Glu Ala Leu Glu His His His His His His
145                 150                 155

<210> SEQ ID NO 3
<211> LENGTH: 137
<212> TYPE: PRT
<213> ORGANISM: Artificial Sequence
<220> FEATURE:
<223> OTHER INFORMATION: synthetic construct

<400> SEQUENCE: 3

Glu Val Gln Leu Gln Ala Ser Gly Gly Gly Leu Val Gln Gly Gly Asp
1               5                   10                  15

Ser Leu Arg Leu Ser Cys Ala Ala Ser Gly Arg Thr Leu Gly Asp Tyr
            20                  25                  30

Gly Val Ala Trp Phe Arg Gln Ala Pro Gly Lys Glu Arg Glu Phe Val
        35                  40                  45

Ser Val Ile Ser Arg Ser Thr Ile Ile Thr Asp Tyr Ala Asn Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Pro Glu Asp Thr Ala Val Tyr Tyr Cys
                85                  90                  95

Ala Val Ile Ala Asn Pro Val Tyr Ala Thr Ser Arg Asn Ser Asp Asp
            100                 105                 110

Tyr Gly His Trp Gly Gln Gly Thr Gln Val Thr Val Ser Ser Ala Ala
        115                 120                 125

Ala Leu Glu His His His His His His
    130                 135

<210> SEQ ID NO 4
<211> LENGTH: 162
<212> TYPE: PRT
<213> ORGANISM: Artificial Sequence
<220> FEATURE:
<223> OTHER INFORMATION: synthetic construct

<400> SEQUENCE: 4

Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Ser Arg Ala
            20                  25                  30

Val Met Gly Trp Phe Arg Gln Ala Pro Gly Lys Glu Arg Glu Phe Val
        35                  40                  45

Ala Ala Ile Ser Ala Ala Pro Gly Thr Ala Tyr Tyr Ala Phe Tyr Ala
    50                  55                  60

Asp Ser Val Arg Gly Arg Phe Ser Ile Ser Ala Asp Ser Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Asp Leu Lys Met Gln Val Ala Ala Tyr Met Asn
             100                 105                 110

Gln Arg Ser Val Asp Tyr Trp Gly Gln Gly Thr Gln Val Thr Val Ser
        115                 120                 125

Ser Ala Ala Ala Asp Pro Asp Asn Glu Ala Tyr Glu Met Pro Ser Glu
130                 135                 140

Glu Gly Tyr Gln Asp Tyr Glu Pro Glu Ala Leu Glu His His His His
145                 150                 155                 160

His His

<210> SEQ ID NO 5
<211> LENGTH: 140
<212> TYPE: PRT
<213> ORGANISM: Artificial Sequence
<220> FEATURE:
<223> OTHER INFORMATION: synthetic construct

<400> SEQUENCE: 5

Glu Val Gln Leu Val Glu Ser Gly Gly Gly Leu Val Gln Ala Gly Asp
1               5                   10                  15

Ser Leu Arg Leu Ser Cys Thr Ala Ser Gly Arg Thr Phe Ser Arg Ala
            20                  25                  30

Val Met Gly Trp Phe Arg Gln Ala Pro Gly Lys Glu Arg Glu Phe Val
        35                  40                  45

Ala Ala Ile Ser Ala Ala Pro Gly Thr Ala Tyr Tyr Ala Phe Tyr Ala
    50                  55                  60

Asp Ser Val Arg Gly Arg Phe Ser Ile Ser Ala Asp Ser Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Ala Asp Leu Lys Met Gln Val Ala Ala Tyr Met Asn
             100                 105                 110

Gln Arg Ser Val Asp Tyr Trp Gly Gln Gly Thr Gln Val Thr Val Ser
        115                 120                 125

Ser Ala Ala Ala Leu Glu His His His His His His
130                 135                 140

<210> SEQ ID NO 6
<211> LENGTH: 160
<212> TYPE: PRT
<213> ORGANISM: Artificial Sequence
<220> FEATURE:
<223> OTHER INFORMATION: synthetic construct

<400> SEQUENCE: 6

Glu Val Gln Leu Gln Ala Ser Gly Gly Gly Leu Val Gln Pro Gly Gly
1               5                   10                  15

Ser Leu Arg Leu Ser Cys Val Ala Ser Gly Ile Asn Phe Ser Thr Asn
            20                  25                  30

Val Pro Thr Trp Tyr Arg Gln Ala Pro Gly Lys Gln Arg Glu Leu Val
        35                  40                  45

Ala Val Ile Thr Thr Asn Gly Leu Thr Arg Tyr Ala Asp Ser Val Lys
    50                  55                  60

Gly Arg Phe Thr Ile Ser Lys Asp Asn Ala Lys Asn Ala Val Tyr Leu
65                  70                  75                  80

Gln Met Asn Ser Leu Lys Pro Glu Asp Thr Ala Val Tyr Tyr Cys Arg
                85                  90                  95

Ala Arg Asp Tyr Trp Gly Gln Gly Thr Gln Val Thr Val Ser Ser Glu
            100                 105                 110

Pro Lys Thr Pro Lys Pro Gln Pro Ala Ala Ser Gly Ala Glu Phe Ala
        115                 120                 125

Ala Ala Asp Pro Asp Asn Glu Ala Tyr Glu Met Pro Ser Glu Glu Gly
        130                 135                 140

Tyr Gln Asp Tyr Glu Pro Glu Ala Leu Glu His His His His His His
145                 150                 155                 160

<210> SEQ ID NO 7
<211> LENGTH: 138
<212> TYPE: PRT
<213> ORGANISM: Artificial Sequence
<220> FEATURE:
<223> OTHER INFORMATION: synthetic construct

<400> SEQUENCE: 7

Glu Val Gln Leu Gln Ala Ser Gly Gly Gly Leu Val Gln Pro Gly Gly
1               5                   10                  15

Ser Leu Arg Leu Ser Cys Val Ala Ser Gly Ile Asn Phe Ser Thr Asn
            20                  25                  30

Val Pro Thr Trp Tyr Arg Gln Ala Pro Gly Lys Gln Arg Glu Leu Val
        35                  40                  45

Ala Val Ile Thr Thr Asn Gly Leu Thr Arg Tyr Ala Asp Ser Val Lys
    50                  55                  60

Gly Arg Phe Thr Ile Ser Lys Asp Asn Ala Lys Asn Ala Val Tyr Leu
65                  70                  75                  80

Gln Met Asn Ser Leu Lys Pro Glu Asp Thr Ala Val Tyr Tyr Cys Arg
                85                  90                  95

Ala Arg Asp Tyr Trp Gly Gln Gly Thr Gln Val Thr Val Ser Ser Glu
            100                 105                 110

Pro Lys Thr Pro Lys Pro Gln Pro Ala Ala Ser Gly Ala Glu Phe Ala
        115                 120                 125

Ala Ala Leu Glu His His His His His His
        130                 135

<210> SEQ ID NO 8
<211> LENGTH: 138
<212> TYPE: PRT
<213> ORGANISM: Artificial Sequence
<220> FEATURE:
<223> OTHER INFORMATION: synthetic construct

<400> SEQUENCE: 8

Glu Val Gln Leu Gln Ala Ser Gly Gly Gly Leu Val Gln Pro Gly Gly
1               5                   10                  15

Ser Leu Arg Leu Ser Cys Val Ala Ser Gly Ile Asn Phe Ser Thr Asn
            20                  25                  30

Val Pro Thr Trp Tyr Arg Gln Ala Pro Gly Lys Gln Arg Glu Leu Val
        35                  40                  45

Ala Val Ile Thr Thr Asn Gly Leu Thr Arg Tyr Ala Asp Ser Val Lys
    50                  55                  60

Gly Arg Phe Thr Ile Ser Lys Asp Asn Ala Lys Asn Ala Val Tyr Leu
65                  70                  75                  80

Gln Met Asn Ser Leu Lys Pro Glu Asp Thr Ala Val Tyr Tyr Cys Arg
                85                  90                  95

Ala Arg Asp Tyr Trp Gly Gln Gly Thr Gln Val Thr Val Ser Ser Glu
            100                 105                 110

-continued

Pro Lys Thr Pro Lys Pro Gln Pro Ala Ala Ser Gly Ala Glu Phe Ala
        115                 120                 125

Ala Ala Leu Glu His His His His His His
    130                 135

<210> SEQ ID NO 9
<211> LENGTH: 135
<212> TYPE: PRT
<213> ORGANISM: Artificial Sequence
<220> FEATURE:
<223> OTHER INFORMATION: synthetic construct

<400> SEQUENCE: 9

Asp Val Gln Leu Gln Ala Ser Gly Gly Gly Leu Ala Gln Ala Gly Gly
1               5                   10                  15

Ser Leu Arg Leu Ser Cys Ala Tyr Ser Gly Asp Thr Val Asn Asp Tyr
            20                  25                  30

Ala Met Ala Trp Phe Arg Gln Ala Pro Gly Lys Gly Arg Glu Phe Val
        35                  40                  45

Ala Ala Ile Arg Ala Arg Gly Gly Thr Glu Tyr Leu Asp Ser Val
    50                  55                  60

Lys Gly Arg Phe Thr Ile Ser Arg Asp Asn Gly Glu Asn Thr Ala Tyr
65                  70                  75                  80

Leu Gln Met Asp Asn Leu Gln Pro Asp Thr Ala Leu Tyr Phe Cys
                85                  90                  95

Ala Leu Ala Met Gly Gly Tyr Ala Tyr Arg Ala Phe Glu Arg Tyr Ser
            100                 105                 110

Val Arg Gly Gln Gly Thr Gln Val Thr Val Ser Ser Ala Ala Ala Leu
        115                 120                 125

Glu His His His His His His
    130                 135

<210> SEQ ID NO 10
<211> LENGTH: 140
<212> TYPE: PRT
<213> ORGANISM: Artificial Sequence
<220> FEATURE:
<223> OTHER INFORMATION: synthetic construct

<400> SEQUENCE: 10

Glu Val Gln Leu Val Glu Ser Gly Gly Gly Leu Val Gln Ala Gly Asp
1               5                   10                  15

Ser Leu Arg Leu Ser Ala Thr Ala Ser Gly Arg Thr Phe Ser Arg Ala
            20                  25                  30

Val Met Gly Trp Phe Arg Gln Ala Pro Gly Lys Glu Arg Glu Phe Val
        35                  40                  45

Ala Ala Ile Ser Ala Ala Pro Gly Thr Ala Tyr Tyr Ala Phe Tyr Ala
    50                  55                  60

Asp Ser Val Arg Gly Arg Phe Ser Ile Ser Ala Asp Ser Ala Lys Asn
65                  70                  75                  80

Thr Val Tyr Leu Gln Met Asn Ser Leu Lys Pro Glu Asp Thr Ala Val
                85                  90                  95

Tyr Tyr Val Ala Ala Asp Leu Lys Met Gln Val Ala Ala Tyr Met Asn
            100                 105                 110

Gln Arg Ser Val Asp Tyr Trp Gly Gln Gly Thr Gln Val Thr Val Ser
        115                 120                 125

Ser Ala Ala Ala Leu Glu His His His His His
    130                 135                 140

```
<210> SEQ ID NO 11
<211> LENGTH: 160
<212> TYPE: PRT
<213> ORGANISM: Artificial Sequence
<220> FEATURE:
<223> OTHER INFORMATION: synthetic construct

<400> SEQUENCE: 11

Glu Val Gln Leu Gln Ala Ser Gly Gly Leu Val Gln Pro Gly Gly
1               5                   10                  15

Ser Leu Arg Leu Ser Ala Val Ala Ser Gly Ile Asn Phe Ser Thr Asn
            20                  25                  30

Val Pro Thr Trp Tyr Arg Gln Ala Pro Gly Lys Gln Arg Glu Leu Val
        35                  40                  45

Ala Val Ile Thr Thr Asn Gly Leu Thr Arg Tyr Ala Asp Ser Val Lys
    50                  55                  60

Gly Arg Phe Thr Ile Ser Lys Asp Asn Ala Lys Asn Ala Val Tyr Leu
65                  70                  75                  80

Gln Met Asn Ser Leu Lys Pro Glu Asp Thr Ala Val Tyr Tyr Val Arg
            85                  90                  95

Ala Arg Asp Tyr Trp Gly Gln Gly Thr Gln Val Thr Val Ser Ser Glu
            100                 105                 110

Pro Lys Thr Pro Lys Pro Gln Pro Ala Ala Ser Gly Ala Glu Phe Ala
            115                 120                 125

Ala Ala Asp Pro Asp Asn Glu Ala Tyr Glu Met Pro Ser Glu Glu Gly
            130                 135                 140

Tyr Gln Asp Tyr Glu Pro Glu Ala Leu Glu His His His His His
145                 150                 155                 160
```